US00PP08301P

United States Patent [19]

Vletter

[11] Patent Number: Plant 8,301

[45] Date of Patent: Jul. 13, 1993

[54] LILY PLANT NAMED GIBRALTAR

[75] Inventor: Floris Vletter, Rijnsburg, Netherlands

[73] Assignee: Gebr. Vletter & J. A. Den Haan, Rijnsburg, Netherlands

[21] Appl. No.: 796,531

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Gibraltar, characterized by its intense orange flower color, large flowers, long stems, vigorous growth habit, and floriferous habit.

1 Drawing Sheet

The present invention comprises a new and distinct cultivar of lily, botanically known as Lilium, known commercially as Lilium Asiatic hybrid, and hereinafter referred to by the cultivar name Gibraltar. The parents were asiatic varieties belonging to division I described in "Classification of Lily Cultivars into Divisions" published by Victoria Mathews, The Royal Botanic Gardens, Kew (1989).

The new cultivar is a product of a planned breeding program which had the primary objectives of creating new lily cultivars with long flexible stems, orange flower color and floriferous habit.

The new cultivar was originated from a hybridization made by the inventor in a controlled breeding program in Rijnsburg, The Netherlands in 1984. Both the male and the female parents are unnamed seedlings.

The new cultivar was discovered and selected as one flowering plant within the progeny of the stated cross by the inventor in June 1984 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Very vigorous growth habit;
2. Strong flower stems;
3. Intense orange flower color;
4. Floriferous habit.

Of the many commercial cultivars known to the present inventor, the most similar in comparison to the new cultivar is the cultivar Eurovision. In comparison to Eurovision, Gibraltar has larger flowers, more intense orange flower color, and longer stems.

The accompanying photographic drawing shows typical flower characteristics of the new cultivar, with colors being as true as possible with illustrations of this type. When flowering is forced under natural light, Gibraltar produces an inflorescence approximately 41 days earlier than Stargazer, grown under the same conditions. Gibraltar is fertile. The photograph comprises a front perspective of flowers fully open, and several buds in various stages.

In the following description, color references are made to The Royal Horticultural Society (R.H.S.) Color Chart. The color values were determined at Wageningen in 1988–1989 and at Rijnsburg in July 1991.

Origin: Seedling from Breeding Program.

Percentage:

*Seed parent.*—Unnamed seedling.

*Pollen parent.*—Unnamed seedling.

Classification:

*Botanical.*—Lilium.

*Commercial.*—Asiatic hybrid.

THE PLANT

Form: A single stem carrying numerous pedicels alternately arranged.

Height: Tall, approximately 130 cm at time of opening of anthers of first flower, depending on growing conditions.

Growth habit: Very vigorous and strong.

Stem: Color 176A; Angular in transverse section; internodal length 1.5 cm and uniform; anthocyanin pigmentation present.

Foliage:

*Quantity.*—75–95 leaves, depending on growing conditions.

*Size of leaf.*—Mature leaves are medium length, 15 cm; width is narrow to very narrow, 1.5 cm.

*Shape to leaves.*—Elliptical.

*Texture.*—Smooth with medium glossiness; no pubescence on lower side.

*Color.*—Medium green 137A.

Bulbs:

*Size.*—Outlet 6–22 cm.

*Color.*—White.

Roots: Both stem and contractile present.

THE BUD

Form: Tapering (like a lancet).
Size: 9 cm prior to opening.
Opening: Unfolds normally.
Color: White 29A with shade of green prior to opening.
Tepals: Folded, three visible.

THE FLOWER

Blooming habit: Raceme.
Size: Approximately 17 cm in diameter, depending on growing conditions.
Borne: Upright.
Shape: Generally in form of hexagonal star.
Tepalage:
*Number of tepals.*—Six.
*Arrangement.*—Three inner and three outer.
*Color.*—Upper surface: Orange 28A. Lower surface: Orange 28B.
*Spotting or marking.*—Dark red spots on inner tepals, the diameter of each of which is approximately 1 mm.
Nectaries and papillae: Present.
Pedicel:

*Length.*—9 cm (first flower).
*Color.*—Medium green.
*Form.*—Strongly curved.
Texture: Ribbed and papillose.
Disease resistance: No disease problems noted to date.
Fragrance: Absent.
Lasting quality: Excellent.

REPRODUCTIVE ORGANS

Stamens, anthers:
*Arrangement.*—Anthers form a generally circular pattern.
*Length.*—Very short to short, 5 cm.
*Number.*—Six.
*Filaments.*—Orange.
Pollen color: Light brown to orange brown.
Anther color: Purple.
Pistils: Orange style; total length of pistil 6.5 cm.
Stigma: Purple red.
Ovaries: Triangular in shape, other characteristics typical asiatic lily varieties.

I claim:

1. A new and distinct cultivar of lily plant named Gibraltar, as illustrated and described.

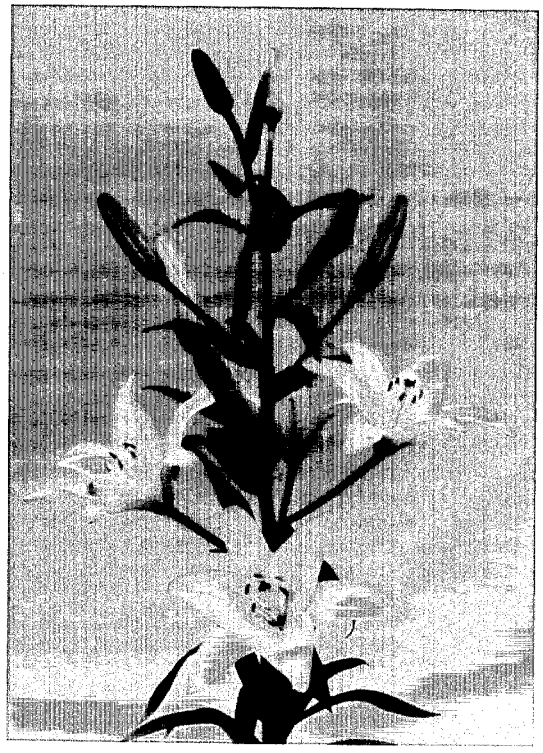

* * * * *